United States Patent

Sartori et al.

[11] Patent Number: 5,859,036
[45] Date of Patent: Jan. 12, 1999

[54] 3,4-DIARYLTHIAZOLIN-2-ONE OR -2-THIONE DERIVATIVES, THEIR METHODS OF PREPARATION AND THEIR USES IN THEIR METHODS OF PREPARATION AND THEIR USES IN THERAPEUTICS

[75] Inventors: Eric Sartori, Paris; Jean-Marie Teulon, La Celle Saint Cloud, both of France

[73] Assignee: Laboratories UPSA, Agen, France

[21] Appl. No.: 962,256

[22] Filed: Oct. 31, 1997

[30] Foreign Application Priority Data

Oct. 7, 1997 [FR] France ................................. 97 12459

[51] Int. Cl.[6] ...................... A61K 31/425; C07D 277/14; C07D 277/16
[52] U.S. Cl. ............................ 514/369; 548/182; 548/186
[58] Field of Search ............................ 514/369; 548/182, 548/186

[56] References Cited

U.S. PATENT DOCUMENTS 5,643,933  7/1997  Talley et al. ............................ 514/372

Primary Examiner—Johann Richter
Assistant Examiner—Jane C. Osweckí
Attorney, Agent, or Firm—Barry J. Marenberg

[57] ABSTRACT

The present invention relates to derivatives of formula

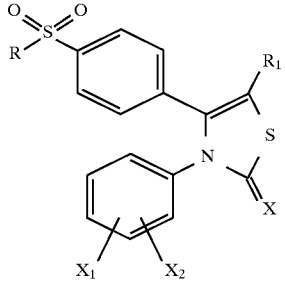

and to their use in therapeutics especially as drugs with anti-inflammatory and analgesic properties.

14 Claims, No Drawings

3,4-DIARYLTHIAZOLIN-2-ONE OR -2-THIONE DERIVATIVES, THEIR METHODS OF PREPARATION AND THEIR USES IN THEIR METHODS OF PREPARATION AND THEIR USES IN THERAPEUTICS

The present invention relates to the 3,4-diarylthiazolin-2-one or -2-thione derivatives of general formula (I) below and their addition salts, particularly pharmaceutically acceptable addition salts, as novel products.

One of the arachidonic acid biotransformation pathways is the cyclooxygenase pathway, which makes it possible to transform arachidonic acid to PGG2 and then PGH2. Recent work on the cloning and sequencing of cyclooxygenase has revealed the presence of two isoenzymes, namely cyclooxygenase-1 (COX-1) and cyclooxygenase-2 (COX-2), in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis which can give rise to side effects. The inhibition of COX-2 will cause a decrease in the prostaglandins produced in an inflammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially in gastric terms. They will be particularly indicated in the treatment of inflammatory phenomena and in the treatment of pain.

An example of their use which may be mentioned is the treatment of arthritis, especially rheumatoid arthritis, spondylitis, gouty arthritis, osteoarthritis, juvenile arthritis, autoimmune diseases and lupus erythematosus. They will also be indicated in the treatment of bronchial asthma, dysmenorrhea, tendinitis, bursitis, dermatological inflammations such as psoriasis, eczema, burns and dermatitis.

They can also be used in the treatment of gastrointestinal inflammations, Crohn's disease, gastritis and ulcerative colitis, in the prevention of cancer, especially adenocarcinoma of the colon, in the prevention of neurodegenerative diseases, particularly Alzheimer's disease, in the prevention of stroke and epilepsy, and in the prevention of premature labour.

Their analgesic properties also enable them to be used for any pain symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the method for the preparation of said products and to their application in therapeutics.

The patent WO95/00501 of Merck Frosst Canada Inc. claims phenyl heterocycles as cyclooxygenase inhibitors and among these heterocycles, mention is made of a thiazole ring. However, these known derivatives are very far from the compounds claimed by the Applicant.

In fact, as to the difference of the compounds of the invention, these known derivatives comprise two aryl groups in positions 4 and 5, i. e. on two carbon atoms of the thiazole ring.

Now, the Applicant has discovered in a surprising way that thiazole derivatives very different from these known compounds: on the one hand in that they have an oxo or thioxo function in position 2, from where come their denomination as thiazolinone or thiazoline thione, on the other hand, in that they have an aromatic ring in position 3, i. e. not on the carbon atom but on the nitrogen atom of the thiazole ring, and finally in that they have a alkylsutphonylphenyl or benzenesulphonamide group in position 4, have remarkable selective cyclooxygenase-2-inhibiting properties.

3,4-diaryl derivatives of thiazole have already been described in the literature, such as, for example, in the Belgian patent 660,222 of Fuji Photo Film Co, Ltd, however, these derivatives are useful as desensitisers in photography and, as to the difference from the derivatives of the invention, they never have an alkylsulphonyl or sulphonamide group in the para position of the phenyl in position 4 of the thiazole, which are necessary in order to obtain cyclooxygenase-2 inhibiting properties.

The 3,4-diarylthiazolin-2-one or -2-thione derivatives according to the invention are characterised in that they are of the general formula (I):

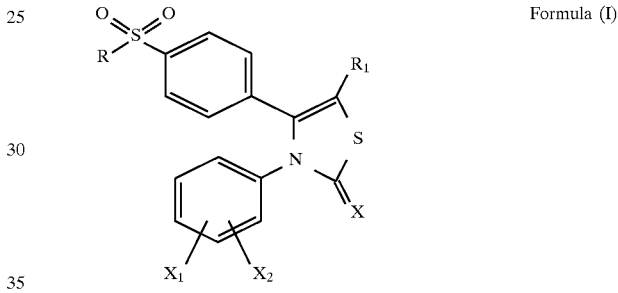

Formula (I)

in which:

R represents:
  a lower alkyl radical having 1 to 6 carbon atoms,
  a lower haloalkyl radical having 1 to 6 carbon atoms, or
  an —NH$_2$ group, R$_1$ represents:
  a hydrogen atom,
  a lower alkyl radical having 1 to 6 carbon atoms, or
  a lower haloalkyl radical having 1 to 6 carbon atoms, X represents:
  an oxygen atom, or
  a sulphur atom, X$_1$ and X$_2$ independently represent:
  a hydrogen atom,
  a halogen atom,
  a lower alkyl radical having 1 to 6 carbon atoms,
  a lower haloalkyl radical having 1 to 6 carbon atoms,
  a lower O-alkyl radical having 1 to 6 carbon atoms, or
  an NR$_2$R$_3$ radical in which R$_2$ and R$_3$ independently represent a lower alkyl radical having 1 to 6 carbon atoms, even X$_1$ and X$_2$ together can form a methylene dioxy group. These derivatives can be in the form of pharmaceutically acceptable addition salts when X$_1$ or X$_2$ has a salifiable function.

In the description and claims, lower alkyl is understood as meaning a linear or branched hydrocarbon chain having 1 to 6 carbon atoms. A lower alkyl radical is for example a methyl, ethyl, propyl, isopropyl, butyl, isobutyl, tert-butyl, pentyl, isopentyl, hexyl, or isohexyl radical.

Lower haloalkyl radical is understood as meaning an alkyl radical having 1 to 6 carbon atoms of which 1 to 7 hydrogen atoms have been substituted with 1 to 7 halogen atoms. A lower haloalkyl radical is for example a trifluoromethyl radical, a 2,2,2-trifluoroethyl radical, a pentafluoroethyl radical, a 2,2-difluoro-3,3,3-trifluoropropyl radical, a heptafluoropropyl radical, or a chloromethyl or bromomethyl radical.

Halogen is understood as meaning a chlorine, bromine, iodine or fluorine atom.

Advantageously, the derivatives in accordance with the invention are derivatives of the above-mentioned formula (I) in which:

R represents:
 a methyl radical, or
 an —NH₂ group,

R₁ represents:
 a hydrogen atom,

X represents:
 an oxygen atom, or
 a sulphur atom,

X₁ and X₂ independently represent:
 a hydrogen atom,
 a halogen atom,
 a lower O-alkyl radical having 1 to 6 carbon atoms,
 a lower alkyl radical having 1 to 6 carbon atoms, or
 an —N(CH₃)₂ radical.

Advantageously, within the context of the present invention, a compound of formula (I) will be used in which at least one of the following conditions is met:

R represents a methyl radical or an —NH₂ group
R₁ represents a hydrogen atom, and
X₁ represents a chlorine atom, a fluorine atom or a bromine atom, and X₂ represents a hydrogen atom, a chlorine atom or a fluorine atom.

The particularly preferred compounds of the invention are those which are selected from the following compounds 4-[3-(3-chloro-4-fluorophenyl)-2-oxo-2,3-dihydro-thiazol-4-yl]-benzenesulphonamide

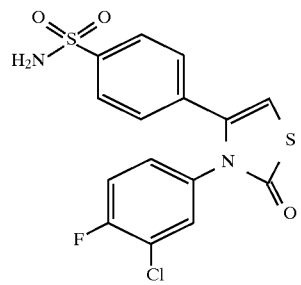

4-[3-(3-fluorophenyl)-2-oxo-2,3-dihydro-thiazol-4-yl]-benzenesulphonamide

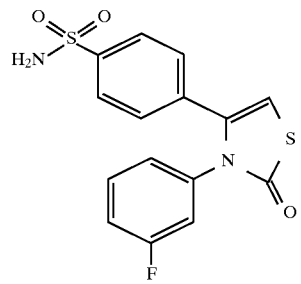

3-(4-chlorophenyl)-4-(4-methanesulphonylphenyl)-3H-thiazol-2-one

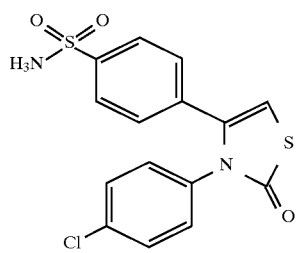

4-[3-(3,4-difluorophenyl)-2-thioxo-2,3-dihydro-thiazol-4-yl]-benzenesulphonamide

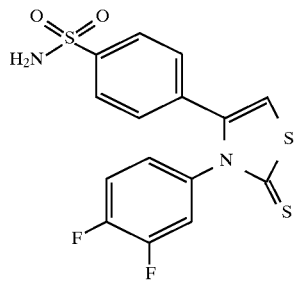

4-[3-(4-bromophenyl)-2-thioxo-2,3-dihydro-thiazol-4-yl]-benzenesulphonamide

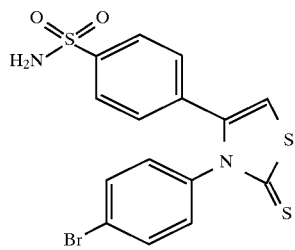

4-[3-(4-chlorophenyl)-2-thioxo-2,3-dihydro-thiazol-4-yl]-benzenesulphonamide

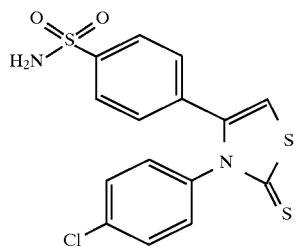

4-[3-(3,4-dichlorophenyl)-2-thioxo-2,3-dihydro-thiazol-4-yl]-benzenesulphonamide

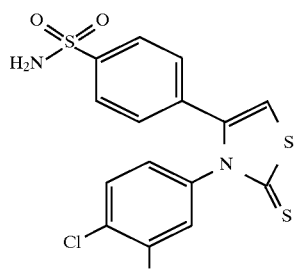

According to the invention, the compounds of formula (I) can be synthesised in the following manner:

The compounds of formula(I) for which X=S can be obtained by dehydration of a 4-hydroxythiazolidin-2-thione of formula (II)

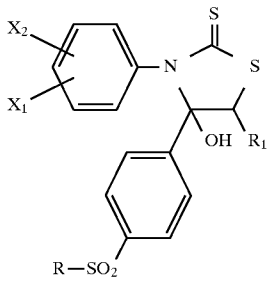

Formula (II)

in which R, $R_1$, $X_1$ and $X_2$ are as defined above, it being possible for this dehydration to be carried out by refluxing in a hydro-alcoholic medium in the presence of an acid, for example in the presence of a mineral acid such as hydrochloric or sulphuric acid, or even in an organic solvent such as toluene or xylene in the presence of paratoluene sulphonic acid, or even in an organic acid such as acetic, trifluoroacetic or propionic acid.

The compounds of formula (II) can be obtained by the action, at ambient temperature, in a solvent such as an alcohol, acetone, tetrahydrofuran or acetonitrile for example, of a phenyldithiocarbamate salt of formula (III)

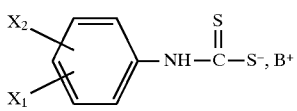

Formula (III)

in which $X_1$ and $X_2$ are as defined above and B+ represents an organic or inorganic cation, such as $Na^+$, $K^+$, $NH_4^+$ or $N(Et)_3H^+$ for example, upon a haloketone of formula (IV)

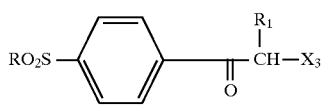

Formula (IV)

in which R and $R_1$ are as defined above and $X_3$ represents a chlorine or bromine atom.

The compounds of formula (III) can be obtained by the action of an aniline

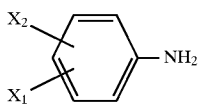

in which $X_1$ and $X_2$ are as defined above, upon carbon disulphide in the presence of a base such as sodium hydroxide, potassium hydroxide, ammonia or triethylamine for example, in an organic solvent such as an alcohol, acetonitrile or tetrahydrofuran, for example.

The compounds of formula (IV) can be obtained by bromination or chlorination of the compounds of formula (V)

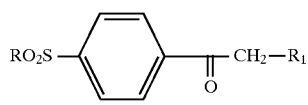

Formula (V)

in which R and $R_1$ are as defined above, this halogenation being carried out with chlorine, bromine, N-chlorosuccinimide or N-bromosuccinimide, for example, in an organic solvent such as methanol or acetic acid, for example.

In the case where R=alkyl, the compounds of formula (V) can be obtained by oxidation of a 4-alkylthiophenylalkanone, with the aid of a peracid, such as, for example, meta-chloroperbenzoic acid in dichloromethane, or an oxidising agent such as oxone in an acetone-water mixture, or even sodium perborate in acetic acid.

In the case where $R=NH_2$, the compounds of formula (V) can be obtained by diazotation of a 4-aminophenylalkanone, followed by the treatment of the diazo obtained with a solution of cupric chloride in acetic acid saturated with sulphur dioxide, then by treating the sulphonyl chloride thus obtained with ammonia in an aqueous or alcoholic medium. It can also be obtained by oxidation of a 4-alkylbenzenesulphonamide, for example by sodium or potassium permanganate in acetone, or by chlorination, for example in refluxing thionyl chloride, of a sodium 4-alkylcarbonylbenzenesulphonate and then reacting with ammonia in aqueous or alcoholic solution.

The compounds of formula (I) for which X=O can be obtained by heating, at the reflux of a haloketone of formula (IV), on a compound of formula (VI)

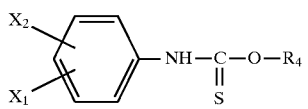

Formula (VI)

in which $X_1$ and $X_2$ are as defined above and $R_4$ is a methyl or ethyl radical, in an organic solvent such as toluene, xylene, an alcohol, tetrahydrofuran, for example. A mixture of compounds is thus obtained of formula (I) wherein X=O and 4-hydroxythiazolidin-2-one of formula (VII)

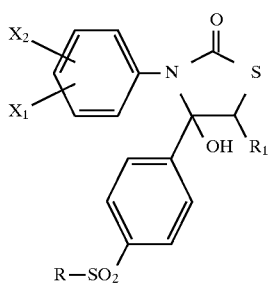

Formula (VII)

in which $X_1$, $X_2$, R and $R_1$ are as defined above, the reaction then being stopped by dehydration by refluxing in a hydro-alcoholic medium in the presence of a mineral acid such as hydrochloric or sulphuric acid, for example, or in an organic solvent such as toluene or xylene in the presence of para-toluenesulphonic acid, or even in an organic acid such as acetic, trifluoroacetic or propionic acid.

The compounds of formula (VI) can be obtained by the action of an aniline of formula

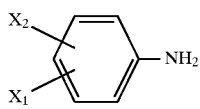

in which $X_1$ and $X_2$ are as defined above, upon bis(ethoxy thiocarbonyl)sulphide or upon bis(ethoxythiocarbonyl) disulphide, according to Sayne, J. Am. Chem. Soc., 1952, p. 3647–3649, in an organic solvent such as methanol or ethanol for example.

Alternatively, the compounds of formula (VI) can be obtained by the action of ethanol or methanol, in the presence or not of sodium ethoxide or methoxide, upon an isothiocyanate of formula

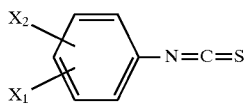

in which $X_1$ and $X_2$ are as defined above.

The compounds of formula (VI) can even be obtained by the treatment of a thiourea of formula

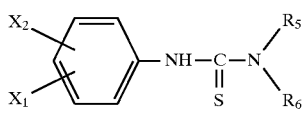

in which $X_1$ and $X_2$ are as defined above and $R_5$ and $R_6$ each independently represent a hydrogen atom, or a lower alkyl radical by refluxing in a hydro-methanolic or hydroethanolic medium in the presence of a mineral acid such as hydrochloric, sulphuric or phosphoric acid.

Finally, the compounds of formula (VI) can also be obtained by treatment of a thiourea of formula

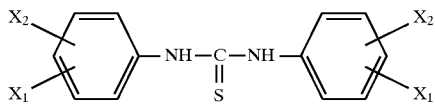

in which $X_1$ and $X_2$ are as defined above, by refluxing in a hydro-methanolic or hydro-ethanolic medium in the presence of a mineral acid such as hydrochloric, sulphuric or phosphoric acid.

The compounds of formula (I) as defined above as well as their addition salts, in particular their pharmaceutically acceptable addition salts, are cyclooxygenase-2 inhibitors and possess a very good anti-inflammatory and analgesic activity coupled with an excellent tolerance, particularly gastric tolerance.

These properties justify their application in therapeutics and the invention further relates, by way of drugs, to the products as defined by formula (I) above as well as their addition salts, in particular their pharmaceutically acceptable addition salts.

The addition salts of certain compounds of formula (I), in particular those which have an acid function, can be obtained by the reaction of these compounds with a base or with an amino acid according to a method known per se. Amongst the bases which can be used, sodium hydroxide, potassium hydroxide, potassium or sodium carbonate and sodium or potassium bicarbonate can be mentioned, and amongst the amino acids, lysine for example.

Thus, the invention also covers a pharmaceutical composition characterised in that it comprises a pharmaceutically effective amount of at least one compound of formula (I) such as defined above or one of its pharmaceutically acceptable addition salts incorporated in a pharmaceutically acceptable excipient, vehicle or carrier.

These compositions can be administered by the buccal, rectal, parenteral, transdermal, ocular, nasal or auricular route.

These compositions can be solid or liquid and can be presented in the pharmaceutical forms commonly used in human medicine, for example simple or coated tablets, gelatine capsules, granules, suppositories, injectable preparations, transdermal systems, eye drops, aerosols and sprays, and ear drops. They are prepared by the customary methods. The active principle, which consists of a pharmaceutically effective amount of at least one compound of formula (I) as defined above or one of its pharmaceutically acceptable addition salts can be incorporated therein together with excipients normally employed in pharmaceutical compositions, such as talc, gum arabic, lactose, starch, magnesium stearate, polyvidone, cellulose derivatives, cocoa butter, semi-synthetic glycerides, aqueous or non-aqueous vehicles, fats of animal or vegetable origin, glycols, various wetting agents, dispersants or emulsifiers, silicone gels, certain polymers or copolymers, preservatives, flavourings and colours.

The invention also covers a pharmaceutical composition with anti-inflammatory and analgesic activity which can be used especially as a favourable treatment for inflammatory phenomena and pain, said composition being characterised in that it comprises a pharmaceutically effective amount of at least one compound of formula (I) above or one of its pharmaceutically acceptable addition salts incorporated in a pharmaceutically acceptable excipient, vehicle or carrier.

In one embodiment, a pharmaceutical composition with anti-inflammatory and analgesic activity is prepared which may be used especially as a favourable treatment for various inflammations and pain.

The invention also covers a pharmaceutical composition useful in the prevention of cancer, in particular adenocarcinoma of the colon, in the prevention of neurodegenerative diseases, particularly Alzheimer's disease, in the prevention of stroke and epilepsy, and in the prevention of premature labour.

In one implementation variant, a composition is formulated as gelatine capsules or tablets containing a dose of 1 mg to 1000 mg, or as injectable preparations containing a dose of 0.1 mg to 500 mg. It is also possible to use compositions formulated as suppositories, ointments, creams, gels, aerosol preparations, transdermal preparations or plasters.

The invention also covers a method of therapeutic treatment for mammals, characterised in that a therapeutically effective amount of at least one compound of formula (I) as defined above or one of its pharmaceutically acceptable addition salts is administered to the said mammal. In one variant of this method of treatment, the compound of formula (I) either by itself or in association with a pharmaceutically acceptable excipient, is formulated as gelatine capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favourable treatment for inflammatory phenomena and pain.

In human and animal therapeutics, the compounds of formula (I) can be administered by themselves or in association with a physiologically acceptable excipient, in any form, in particular orally in the form of gelatine capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatine capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly by reading the following Examples, which in no way imply a limitation but are given by way of illustration.

EXAMPLE 1

(4-methanesulphonylphenyl)-ethanone $R=CH_3, R_1=H$        Formula (V)

A solution of 1036 g of oxone and 11.7 g of EDTA (Ethylene diamine tetraacetic acid) dissolved in 3.8 l of water is added dropwise to a solution of (4-methylthiophenyl)ethanone (prepared according to J. Am. Chem. Soc. 1952 p. 5475) in 1 l of acetone and 1.1 l of water, the temperature being kept below 32° C. The reaction mixture is stirred for 16 h after the end of the addition, then 550 g of sodium metabisulphite are added portionwise. The reaction mixture is then filtered, the solid obtained is taken up in water, dried in the oven and recrystallised from ethanol.

Yield 165 g, 78%, melting point 128° C.

EXAMPLE 2

2-bromo-1-(4-methanesulphonylphenyl)-ethanone $R=CH_3, R_1=H, X_3=Br$      Formula (IV)

38.5 ml of bromine dissolved in 110 ml of acetic acid are added dropwise onto a suspension of 159 g of the product of Example 1 in 1.6 l of acetic acid and 1.6 ml of hydrochloric acid, the reaction mixture is then stirred for 3 h at ambient temperature. The precipitate obtained is filtered, rinsed with water and then dissolved in dichloromethane and dried over magnesium sulphate. The dichloromethane is evaporated off, the residue is taken up in pentane and filtered to give 100 g of the expected product. A second batch is obtained by pouring the filtrate of the reaction mixture onto an ice/water mixture, then by filtering off and by treating the precipitate as previously. The two batches are then combined and recrystallised from acetic acid.

Yield 143 g, 64%, melting point 130° C.

EXAMPLE 3

4-acetylbenzenesulphonyl chloride 100 g of para-amino acetophenone are dissolved in 124 ml of concentrated hydrochloric acid and the mixture is cooled to 0° C. A solution of 55.2 g of sodium nitrite in 90 ml of water are then added in keeping the temperature at 0° C. After 1 h of stirring, the solution obtained is added dropwise to a solution of 23 g of cupric chloride in 600 ml of glacial acetic acid saturated with sulphur dioxide. After stirring for 1 h at ambient temperature, the reaction mixture is poured into 2 l of ice-water mixture, then filtered off. The orange solid obtained is washed with water, then with pentane.

Yield 136 g, 84%, melting point 186° C.

EXAMPLE 4

4-acetylbenzenesulphonamide $R=NH_2, R_1=H$        Formula (V)

131 g of product of Example 3 are added portionwise to 1 l of ethanol saturated with ammonia. The reaction mixture is stirred at ambient temperature for 24 h, then concentrated and water is added thereto. The solid obtained is filtered, then washed with isopropanol and pentane.

Yield 90.3 g, 76%, melting point 181° C.

EXAMPLE 5

4-bromoacetylbenzenesulphonamide $R=NH_2, R_1=H, X_3=Br$      Formula (IV)

90.3 g of the product of Example 4 are dissolved in 900 ml of methanol, 0.9 g of benzoyl peroxide are then added and 24 ml of bromine are added dropwise. The mixture is stirred under ultra-violet irradiation for 24 h, at ambient temperature, then concentrated. The residue is taken up in water, filtered off, washed with isopropanol and pentane.

Yield 111.4 g, 88%, melting point 156° C.
(literature 130°–132° C., Fujikura T., Chem. Pharm. Bull. 1982, p.4092–4101)

EXAMPLE 6

Triethylammonium 3-chlorophenyldithiocarbamate $X_1=3\text{-Cl}, X_2=H, B^+=HN^+(Et)_3$    Formula (III)

5.7 g of carbon disulphide and 22 ml of triethylamine are mixed in keeping a temperature below 10° C. by an ice-bath. 10 g of 3-chloroaniline dissolved in 10 ml of absolute ethanol are added and the reaction mixture is stirred and left to return to ambient temperature. After 24 h, the yellow precipitate obtained is filtered off, washed with ethanol then with pentane.

Yield 22.9 g, 96%, melting point 86° C.

EXAMPLE 7

4-[3-(3-chlorophenyl)-4-hydroxy-2-thioxo-thiazolidin-4-yl]-benzenesulphonamide $X_1=3\text{-Cl}, X_2=H, R=NH_2, R_1=H$    Formula (II)

5 g of the product of Example 5 and 5.5 g of the product of Example 6 are dissolved in 60 ml of acetonitrile, and the mixture is stirred for 5 h at ambient temperature. It is then poured into 500 ml of water, extracted with dichloromethane, the dichloromethane phase is then washed with water, then dried over magnesium sulphate and evaporated off. The solid obtained is taken up in ether and filtered.
Yield 5.4 g, 82%, melting point 156° C.

EXAMPLE 8

4-[3-(3-chlorophenyl)-2-thioxo-2,3-dihydro-thiazol-4-yl]-benzenesulphonamide $X=S$, $X_1=3$-Cl, $X_2=H$, $R=NH_2$, $R_1=H$     Formula (I)

5.4 g of the product of Example 7 are dissolved in 50 ml of ethanol to which 1 ml of concentrated hydrochloric acid has been added. The reaction mixture is refluxed for 1 h, then filtered. The solid obtained is washed with ethanol, then with pentane.
Yield 3 g, 58%, melting point 255° C.

The products of Examples 9 to 31 were obtained from the corresponding triethylammonium phenyldithiocarbamates and the products of the Examples 2 and 5, according to the methods of Examples 7 and 8. The intermediate 4-hydroxythiazolidinones were used without prior purification, and the yield indicated is the overall yield of the steps corresponding to Examples 7 and 8.

| Example | R | $X_1$ | $X_2$ | Yld | MPt |
|---|---|---|---|---|---|
| 9  | $CH_3$ | 3-Cl | H | 51% | 269° C. |
| 10 | $NH_2$ | 3-Cl | 4-Cl | 30% | 235° C. |
| 11 | $NH_2$ | 4-Cl | H | 35% | 243° C. |
| 12 | $NH_2$ | 3-F | 4-Cl | 18% | 210° C. |
| 13 | $NH_2$ | 4-F | H | 48% | 270° C. |
| 14 | $NH_2$ | 4-$CH_3$ | H | 17% | 275° C. |
| 15 | $CH_3$ | 3-Cl | 4-Cl | 28% | 235° C. |
| 16 | $CH_3$ | 4-Cl | H | 20% | 230° C. |
| 17 | $NH_2$ | 4-I | H | 42% | >275° C. |
| 18 | $NH_2$ | 4-Br | H | 51% | >275° C. |
| 19 | $NH_2$ | 3-Cl | 4-I | 43% | 248° C. |
| 20 | $NH_2$ | 3-Cl | 4-$OCH_3$ | 22% | 228° C. |
| 21 | $NH_2$ | 3-Cl | 4-$CH_3$ | 32% | 218° C. |
| 22 | $CH_3$ | 4-F | H | 20% | 186° C. |
| 23 | $CH_3$ | 3-F | H | 43% | 255° C. |
| 24 | $NH_2$ | 4-$N(CH_3)_2$, HCl | H | 34% | 280–285° C. |
| 25 | $CH_3$ | 3-F | 4-F | 56% | 240° C. |
| 26 | $CH_3$ | 3-Cl | 4-Br | 56% | 246° C. |
| 27 | $CH_3$ | 3-Cl | 4-F | 68% | 277° C. |
| 28 | $CH_3$ | 4-$N(CH_3)_2$, HCl | H | 57% | 235° C. |
| 29 | $NH_2$ | 3-F | H | 33% | 221° C. |
| 30 | $NH_2$ | 3-F | 4-F | 32% | 265° C. |
| 31 | $NH_2$ | 3-$CH_3$ | H | 26% | 271° C. |

EXAMPLE 32

O-Ethyl p-tolylthiocarbamate $X_1=4$-$CH_3$, $X_2=H$, $R_4=CH_2$–$CH_3$     Formula (VI)

2.5 g of p-toluidine and 5 g of bis(ethoxythiocarbonyl) sulphide are dissolved in 50 ml of ethanol and this mixture is stirred at ambient temperature for 24 h. The ethanol is evaporated off and the residue is taken up in pentane giving a white solid.
Yield: 3.7 g, 80%, melting point 84° C.
(Lit. 87° C., Greifenhagen W., J. Am. Chem. Soc.,1943, p.900)

EXAMPLE 33

Mixture of 4-[4-hydroxy-3-(4-methylphenyl)-2-oxothiazolidin-4-yl]-benzenesulphonamide and 4-[3-(4-methylphenyl)-2-oxo-2,3-dihydro-thiazol-4-yl] benzenesulphonamide $X_1=4$-$CH_3$, $X_2=H$, $R=NH_2$, $R_1=H$     Formula (VII)

$X=O$, $X_1=4$-$CH_3$, $X_2=H$, $R=NH_2$, $R_1=H$     Formula (I)

3.7 g of the product of Example 32 and 5.2 g of the product of Example 5 are dissolved in 40 ml of tetrahydrofuran and the mixture is refluxed for 8 h. A slight insoluble is filtered, the solvent is then evaporated off and the residue taken up in dichloromethane and washed with water. The organic solution is dried over magnesium sulphate, then evaporated and the residue is crystallised from ether giving a white solid.
Yield 4.5 g, 65%

EXAMPLE 34

4-[3-(4-methylphenyl)-2-oxo-2,3-dihydro-thiazol-4-yl]-benzenesulphonamide $X=O$, $X_1=4$-$CH_3$, $X_2=H$, $R=NH_2$, $R_1=H$     Formula (I)

4.5 g of the product of Example 33 are dissolved in 500 ml of ethanol to which 1 ml of concentrated hydrochloric acid has been added. The reaction mixture is refluxed for 1 h 30, then left to return to ambient temperature. The precipitate obtained is filtered off, washed with ethanol then with pentane giving a cream-coloured solid.
Yield 3.2 g, 75%, melting point 219° C.

The products of the Examples 35 to 46 were obtained from the corresponding phenylthiocarbamic acid O-ethyl esters and the products of the Examples 2 and 5, according to the methods of Examples 33 and 34.

$X=O$, $R_1=H$     Formula (I)

| Example | R | $X_1$ | $X_2$ | Yld | MPt |
|---|---|---|---|---|---|
| 35 | $CH_3$ | 3-Cl | 4-Cl | 25% | 191° C. |
| 36 | $NH_2$ | 3-F | 4-F | 49% | 213° C. |
| 37 | $NH_2$ | 3-$CH_3$ | H | 75% | 191° C. |
| 38 | $NH_2$ | 3-Cl | 4-$CH_3$ | 50% | 195° C. |
| 39 | $NH_2$ | 3-Cl | 4-Cl | 37% | 164° C. |
| 40 | $NH_2$ | 3-F | 4-$CH_3$ | 28% | 171° C. |
| 41 | $CH_3$ | 3-Cl | 4-F | 59% | 200° C. |
| 42 | $CH_3$ | 3-F | 4-F | 51% | 184° C. |
| 43 | $CH_3$ | 3-Cl | H | 59% | 173° C. |
| 44 | $NH_2$ | 3-Cl | 4-F | 46% | 198° C. |
| 45 | $NH_2$ | 3-F | H | 73% | 197° C. |
| 46 | $CH_3$ | 4-Cl | H | 60% | 220° C. |

PHARMACOLOGY

The anti-inflammatory activity of the compounds of the Examples has been evaluated according to the method of oedema with carrageenan and the analgesic activity has been evaluated according to the method of arthritis with kaolin.

Methods

Anti-inflammatory activity:

The anti-inflammatory activity is evaluated in rats by the test of oedema with carrageenan. The product is administered orally at a rate of 2.5 ml/100 g (n=6 animals per dose) 2 hours 30 minutes after a water overload taken orally (2.5 ml/100 g). One hour after administration of the product, the oedema is induced by plantar subcutaneous injection of aqueous 2% carrageenan solution. The results are expressed as $ID_{50}$, dose in mg/kg, calculated by linear regression, which induces 50% of the maximal decrease of the volume of the oedema obtained from each product tested.

Analgesic activity:

The analgesic activity is evaluated in rats by the test of arthritis with kaolin. Thirty minutes after intra-articular administration of an aqueous 10% suspension of kaolin, the product is administered orally at a rate of 1 ml/ 100 g (n=10 animals per dose). The results are expressed in the form of $ED_{50}$, the dose in mg/kg which induces 50% decrease of the maximal quotations obtained in the control batch, calculated by linear regression.

| Example | Anti-inflammatory Activity $ID_{50}$ (mg/kg) | Analgesic activity $ED_{50}$ (mg/kg) |
|---|---|---|
| 45 | 2.8 | 1.3 |

Inhibition of the COX-1 and COX-2 enzymatic activities

The molecule studied is preincubated for 10 minutes at 25° C. with 2 U of COX-1 (purified enzyme from ram seminal vesicles) or 1 U of COX-2 (purified enzyme from ewe placenta). Arachidonic acid (6 $\mu$M for COX-1,4 $\mu$M for COX-2) is added to the reaction medium and incubation is carried out for 5 minutes at 25° C. When incubation has ended, the enzymatic reaction is stopped by the addition of 1 N HCl and the PGE2 produced is determined by EIA.

The results are expressed in the form of $IC_{50}$, concentration in gm corresponding to 50% inhibition of the maximal enzymatic activity upon COX-1 and COX-2 (n=1 to 4 determinations).

| Example | COX-2 inhibition $IC_{50}$ ($\mu$M) | COX-1 inhibition $IC_{50}$ ($\mu$M) | Selectivity COX-1/COX-2 ratio |
|---|---|---|---|
| 9 | 3.34 | 100 | 30 |
| 13 | 0.93 | 32 | 34 |
| 20 | 2 | 17.6 | 9 |
| 29 | 0.65 | 258 | 396 |
| 30 | 0.21 | 19.8 | 94 |
| 39 | 0.14 | 1.94 | 14 |
| 45 | 0.24 | 335 | 1367 |
| 46 | 0.57 | 163 | 286 |

TOXICOLOGY

The first toxicology studies performed show that the products of the Examples do not induce a deleterious effect in the rat after the oral absorption of doses ranging up to 300 mg/kg.

What is claimed is:

1. 3,4-diarylthiazolin-2-one or 2-thione compounds of the formula (I):

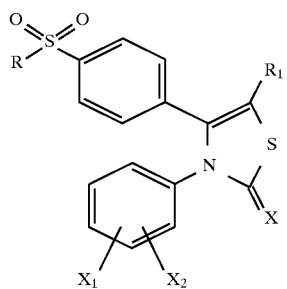

Formula (I)

in which:
R represents:
  a lower alkyl radical having 1 to 6 carbon atoms,
  a lower haloalkyl radical having 1 to 6 carbon atoms, or
  an —NH$_2$ group,
$R_1$ represents:
  a hydrogen atom,
  a lower alkyl radical having 1 to 6 carbon atoms, or
  a lower haloalkyl radical having 1 to 6 carbon atoms,
X represents:
  an oxygen atom, or
  a sulphur atom,
$X_1$ and $X_2$ independently represent:
  a hydrogen atom,
  a halogen atom,
  a lower alkyl radical having 1 to 6 carbon atoms,
  a lower haloalkyl radical having 1 to 6 carbon atoms,
  a lower O-alkyl radical having 1 to 6 carbon atoms, or
  an NR$_2$R$_3$ radical in which R$_2$ and R$_3$ independently represent a lower alkyl radical having 1 to 6 carbon atoms,
or even $X_1$ and $X_2$ together can form a methylene dioxy group, as well as their addition salts.

2. The compounds of formula (I) according to claim 1, in which:
R represents:
  a methyl radical, or
  an —NH$_2$ group,
$R_1$ represents:
  a hydrogen atom,
X represents:
  an oxygen atom, or
  a sulphur atom,
$X_1$ and $X_2$ independently represent:
  a hydrogen atom,
  a halogen atom,
  a lower alkyl radical having 1 to 6 carbon atoms,
  a lower O-alkyl radical having 1 to 6 carbon atoms, or
  an —N(CH$_3$)$_2$ radical, as well as their addition salts.

3. The compounds according to claim 1, in which R represents a methyl radical or an —NH$_2$ group.

4. The compounds according to claim 1, in which $R_1$ is a hydrogen atom.

5. The compounds according to claim 1, in which $X_1$ represents a chlorine atom, a fluorine atom or a bromine atom, and $X_2$ represents a hydrogen atom, a chlorine atom or a fluorine atom.

6. The compounds according to claim 1, which they are selected from the group consisting of the following compounds:

4-[3-(3-chloro-4-fluorophenyl)-2-oxo-2,3-dihydro-thiazol-4-yl]-benzenesulphonamide

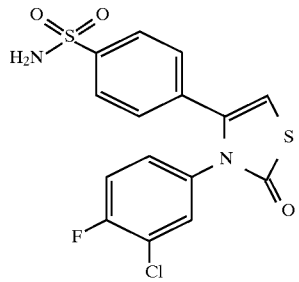

4-[3-(3-fluorophenyl)-2-oxo-2,3-dihydro-thiazol-4-yl]-benzenesulphonamide

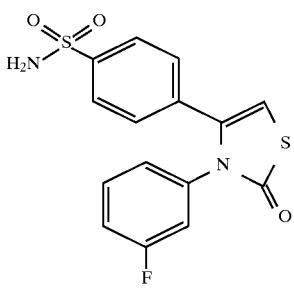

3-(4-chlorophenyl)-4-(4-methanesulphonylphenyl)-3H-thiazol-2-one

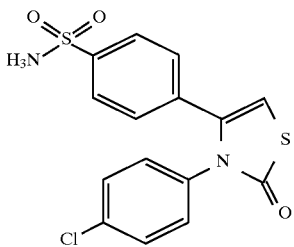

4-[3-(3,4-difluorophenyl)-2-thioxo-2,3-dihydro-thiazol-4-yl]-benzenesulphonamide

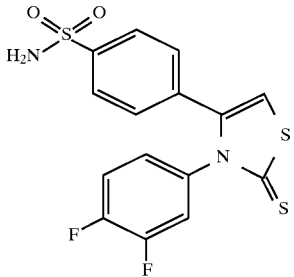

4-[3-(4-bromophenyl)-2-thioxo-2,3-dihydro-thiazol-4-yl]-benzenesulphonamide

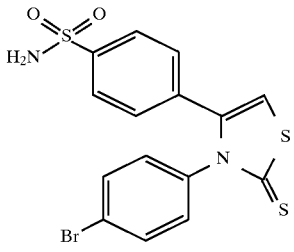

4-[3-(4-chlorophenyl)-2-thioxo-2,3-dihydro-thiazol-4-yl]-benzenesulphonamide

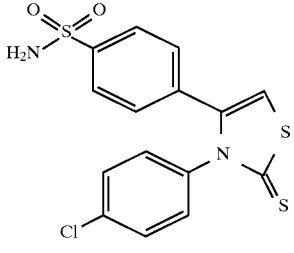

4-[3-(3,4-dichlorophenyl)-2-thioxo-2,3-dihydro-thiazol-4-yl]-benzenesulphonamide

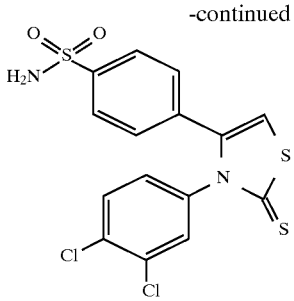

7. A method of preparing compounds of formula (I) according to claim 1, which comprises the reaction of a haloketone of formula (IV)

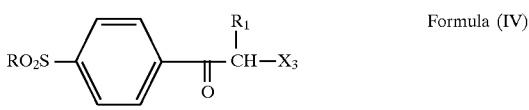

in which R and $R_1$ are as defined in claim 1 and $X_3$ represents a bromine atom or a chlorine atom with a compound of formula (III)

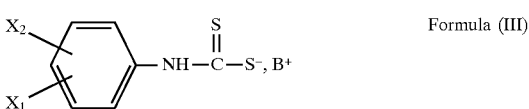

in which $X_1$ and $X_2$ are as defined in claim 1 and B+ represents an organic or inorganic cation, or with a compound of formula (VI)

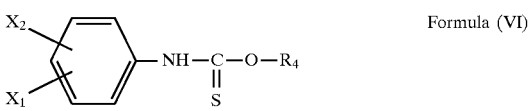

in which $X_1$ and $X_2$ are as defined in claim 1 and $R_4$ represents a methyl or ethyl radical in a solvent, at a temperature between ambient and the reflux of the solvent used and the dehydration of the product of the cyclisation thus obtained by refluxing in a hydro-alcoholic medium.

8. A pharmaceutical composition, which comprises a pharmaceutically effective amount of at least one compound of formula (I) as defined in claim 1, or one of its pharmaceutically acceptable addition salts incorporated in a pharmaceutically acceptable excipient, vehicle or support.

9. A pharmaceutical composition with anti-inflammatory and analgesic activity, which comprises a pharmaceutically effective amount of a compound of formula (I) as defined in claim 1, or a pharmaceutically acceptable salt thereof, incorporated in a pharmaceutically acceptable excipient, vehicle or carrier.

10. A pharmaceutical composition useful in the treatment of cancer, in the treatment of neurodegenerative diseases, in the prevention of stroke and epilepsy, and in the prevention of premature labour, which comprises a pharmaceutically effective amount of a compound of formula (I) such as defined in claim 1, or a pharmaceutically acceptable addition salt thereof, incorporated in a pharmaceutically acceptable excipient, vehicle or support.

11. A pharmaceutical composition according to claim 8, which is presented in the form of gelatine capsules or tablets containing a dose of 1 mg to 1000 mg.

12. A pharmaceutical composition according to claim 8, which is presented in the form of an injectable preparation containing a dose of 0.1 mg to 500 mg.

13. A method for the treatment of inflammation in a mammal which comprises administering an anti-inflammatory effective amount of a compound of formula (I) as defined in claim 1 or a pharmaceutically acceptable salt thereof to said mammal.

14. A method for the treatment of pain in a mammal which comprises administering an effective amount of a compound of formula (I) as defined in claim 1 or a pharmaceutically acceptable salt thereof to said mammal.

* * * * *

UNITED STATES PATENT AND TRADEMARK OFFICE
CERTIFICATE OF CORRECTION

PATENT NO. : 5,859,036
DATED : January 29, 1999
INVENTOR(S) : Eric Sartori, et al.

It is certified that error appears in the above-identified patent and that said Letters Patent is hereby corrected as shown below:

On the title page, item [56] and column 1 line 1, the title should read --

3,4-DIARYLTHIAZOLIN-2-ONE OR -2-THIONE DERIVATIVES, THEIR METHODS OF PREPARATION AND THEIR USES IN THERAPEUTICS

Signed and Sealed this

First Day of June, 1999

Attest:

Q. TODD DICKINSON

Attesting Officer

Acting Commissioner of Patents and Trademarks